United States Patent [19]
Kurtz et al.

[11] Patent Number: 5,660,719
[45] Date of Patent: Aug. 26, 1997

[54] ULTRAVIOLET LIGHT APPARATUS FOR FLUID PURIFICATION

[76] Inventors: Mark E. Kurtz, P.O. Box 1707, Rutland, Vt. 05701-1707; Paul Albertazzi, Currier Rd., Killington, Vt. 05751

[21] Appl. No.: 363,527

[22] Filed: Dec. 23, 1994

[51] Int. Cl.⁶ ........................................................ C02F 1/48
[52] U.S. Cl. .................... 210/85; 210/748; 422/24; 422/186.3; 250/432 R; 250/436
[58] Field of Search ..................... 210/748, 85; 422/24, 422/186.3; 250/432 R, 435–438

[56] References Cited

U.S. PATENT DOCUMENTS

| | | |
|---|---|---|
| 4,518,895 | 5/1985 | Lehman . |
| 4,968,489 | 11/1990 | Peterson . |
| 4,971,687 | 11/1990 | Anderson . |
| 5,006,244 | 4/1991 | Maarschalkerweerd . |
| 5,019,256 | 5/1991 | Ifill et al. . |
| 5,133,945 | 7/1992 | Hallett . |
| 5,151,174 | 9/1992 | Wiesmann . |
| 5,186,907 | 2/1993 | Yanagi et al. . |
| 5,208,461 | 5/1993 | Tipton . |
| 5,332,388 | 7/1994 | Schuerch et al. ................. 422/291 |
| 5,368,826 | 11/1994 | Weltz et al. ..................... 422/243 |

FOREIGN PATENT DOCUMENTS

| | | |
|---|---|---|
| 1163086 | 3/1984 | Canada . |
| 0232274 | 11/1985 | Japan . |
| 2016767 | 1/1987 | Japan . |
| 2071533 | 4/1987 | Japan . |

*Primary Examiner*—Neil McCarthy
*Attorney, Agent, or Firm*—Law Offices of Kenneth F. Dusyn

[57] ABSTRACT

An apparatus for the treatment of a fluid is provided which includes a separate housing and enclosure for containing at least one ballast and electrical means, respectively, to power and control the operation of a plurality of vertically arranged UV lamps that are immersed in a fluid to be treated. Each compartment serves as an individually isolated area for offering greatly enhanced accessibility, maintenance and maximum performance of the various components of an ultraviolet light purification apparatus in the environment intended for its operation and use.

78 Claims, 7 Drawing Sheets

ULTRAVIOLET LIGHT APPARATUS FOR FLUID PURIFICATION

BACKGROUND OF THE INVENTION

1. Field of the Invention

The present invention relates to an ultraviolet light apparatus for the purification of a fluid, and more particularly to a module that employs a particular arrangement of ballasts, electronics and at least one ultraviolet lamp for the treatment of a fluid, such as waste water, by destroying undesirable bacteria and microorganisms.

2. Related Art

U.S. Pat. No. 5,019,256 issued to Ifill et al. on May 28, 1991 discloses a UV lamp rack assembly comprising a vertical array of horizontally disposed UV lamp units for the treatment of wastewater wherein each UV lamp unit can be separately removed. A power control panel is provided at a location remote from the rack assembly for the inclusion of ballasts and various electronics to control the operation of the lamp units. The patent indicates that the ballasts may alternatively be housed in a submerged waterproof enclosure located immediately above the lamp units and below a deflector D that is shown in FIGS. 2, 3 and 5, or that the ballasts and some electronic circuits can be housed in a conduit forming part of the frame for the lamp rack.

U.S. Pat. No. 5,133,945 issued to Hallett on Jul. 28, 1992 discloses a brush device for cleaning the protective quartz sheath of a high intensity, high temperature, vertically aligned UV lamp reactor used for treating a fluid medium. The UV lamp reactor is provided with a fan to direct cooling air onto the ceramic mounting portion of the lamp end. However, the required ballasts and electronics for powering and controlling the reactor are not included with the reactor apparatus and the patent is silent with regard to their disposition and location.

U.S. Pat. No. 5,151,174 issued to Weismann on Sep. 29, 1992 discloses a UV irradiation apparatus for disinfecting clarified sewage comprising a plurality of UV radiators which are grouped together to form modular, individually replaceable, radiator groups (FIG. 2) that are mounted into a siphon (FIG. 1) such that the groups are arranged in a plane which is perpendicular to the direction of sewage flow. Electrical fittings for operating the UV radiators are arranged at the upper side of each radiator group, although there is no indication as to the positioning or location of ballasts that are required for powering the radiator groups of lamps. The patent further indicates that the siphon and its hydraulic fittings, electrical fittings, and an electric supply system for the operation of the apparatus, can all be designed as a compact modular unit. However, no disclosure is offered regarding the details of such a module.

U.S. Pat. No. 5,006,244 issued to Maarschalkerweerd on Apr. 9, 1991 discloses a vertical array of horizontally disposed UV lamps between two parallel frame legs that serve as a conduit for the passage and containment of electrical lead wires leading from a ballast to the individual lamp sockets. The ballast is incorporated with a horizontal frame member that connects the frame legs.

SUMMARY OF THE INVENTION

In its broadest aspect, the present invention provides an apparatus that includes a separate housing and enclosure for containing at least one ballast and electrical means, respectively, to power and control the operation of a plurality of vertically arranged UV lamps that are immersed in a fluid for the treatment of the fluid. By housing the ballast and electrical means in compartments that are separate from each other, and providing the ballast and electrical means with detachable electrical couplers, each compartment serves as an individually sealed and isolated area for offering greatly enhanced accessibility, maintenance and maximum performance of the various components of an ultraviolet light (hereinafter referred to as "UV") purification apparatus in the environment intended for its operation and use.

More specifically, the invention provides an ultraviolet light apparatus for the treatment of a fluid comprising a plurality of vertically arranged ultraviolet lamps accompanied by appropriate means to permit submersion of the lamps in the fluid to be treated. The UV apparatus further includes a housing for containing at least one ballasts to power the lamps, although a plurality of ballasts is typically utilized. At least one enclosure is provided for containing electrical means that serve to operate the lamps by furnishing communication between the ballast and lamps. The enclosure is disposed intermediate the housing and plurality of UV lamps. The housing, enclosure and plurality of lamps are preferably vertically aligned relative to each other, to simplify access to the housing and enclosure. Each of these members are also preferably arranged to interface each other.

Each of the lamps is vertically aligned with the enclosure. In order to prevent the fluid from accessing the electrical connections, the means for permitting the lamps to be submerged in the fluid includes a radiation pervious protective sleeve, preferably made of quartz, disposed about each lamp, one end of which is closed and the other end secured within the enclosure in waterproof relationship thereto. The enclosure is sealed to provide a water-resistant atmosphere for the electrical means therein, preferably with a waterproof seal to prevent the substantial entrainment of moisture in the enclosure thereby offering a dry environment for the enclosed electrical means.

Inasmuch as a substantial amount of heat is generated during the functioning of the ballast, the housing is provided with a means for cooling the ballast which in one embodiment comprises at least one opening in the housing for the passage of ambient air therethrough, and preferably the addition of at least one fan operatively communicating with the opening for the circulation of ambient air in the housing. Alternatively, the housing may be provided with an air conditioning means as a means for cooling the ballasts, or a sealed heat exchanger. By utilizing the air conditioning means or heat exchanger, the housing is configured to be closed to ambient air.

The electrical means, which is housed in the enclosure, includes lead wires connecting the UV lamp ends with detachable couplers also disposed within the enclosure. In similar fashion, the ballast, which is compartmentalized in its own housing, includes lead wires connected to detachable couplers disposed within the housing for detachably connecting the ballast to the electrical means. This modular arrangement of the ballast within its housing and the electrical means within its corresponding enclosure permits either one of these components and the UV lamps to be separately addressed or removed while in its operating environment during maintenance operations without materially disturbing the unaffected members of the apparatus.

The electrical means may further include a means for sensing the functional status of at least one, and preferably all, of the lamps, contained within the apparatus. As used herein, the phrase "functional status" is meant to describe whether the lamp is "ON" or "OFF" for the purpose of emitting ultraviolet light, i.e., whether the lamp is or is not emitting ultraviolet light.

Another aspect of the invention contemplates the utilization of an ultraviolet light module for the purification of a fluid, which, in addition to the aforestated UV lamps, housing, enclosure and electrical means, includes a plurality of ballasts for powering the UV lamps, typically on the order of one or two UV lamps per ballast, and a base communicating with a plurality of vertically arranged support legs connected to the enclosure for supporting the UV lamps between the enclosure and base. In this fashion, all of the elements making up the module are integrated into a single unit which can be easily handled and lowered into an appropriately configured channel or conduit containing a body of fluid.

In order to enhance the UV light purification module, a sensing means can be included intermediate the base and enclosure for sensing the intensity of ultraviolet light generated by the lamps. In addition, as part of the electrical means contained within the module enclosure, a means for generating a signal that is reflective of the intensity of the ultraviolet light provided by the sensing means, may be included.

As the fluid to be treated, which is commonly in the form of waste water, flows past the UV lamps, contaminants within the fluid will, over time, adhere to the surface of the protective sleeves surrounding the UV lamps, thereby occluding the ultraviolet light emitted by the lamps. In accordance with another aspect of the invention, the module can optionally include a means for preventing the collection of contaminants onto the sleeve surface. Such a means comprises at least one aperture, preferably a plurality of apertures, disposed in the base of the module communicating with a source of compressed gas (e.g., air or an inert gas such as nitrogen, argon, etc.) for the passage of the gas therethrough into the fluid about the UV lamp in the form of gas-containing bubbles. The gas-containing bubbles rising through the fluid causes agitation of the fluid about the protective sleeve and UV lamp which prevents the residue or contaminants contained in the fluid from collecting onto the sleeve surface. In a preferred embodiment, at least one support leg of the module, preferably a plurality of support legs, serves as a conduit for the passage of the compressed gas to the base. The compressed gas is preferably introduced to the leg support from a source external to the module via a conduit provided in the enclosure communicating with the leg support.

BRIEF DESCRIPTION OF THE DRAWINGS

A complete understanding of the present invention may be obtained by reference to the following specification when taken in conjunction with the accompanying drawings wherein certain preferred embodiments are illustrated and wherein like numerals refer to like parts throughout. Thus.

DETAILED DESCRIPTION OF THE INVENTION AND PREFERRED EMBODIMENTS THEREOF

The present invention provides a UV light apparatus, preferably in the form of a module, for the purification and treatment of a fluid which upon exposure to a plurality of vertically arranged UV lamps will destroy harmful bacteria and microorganisms contained within the body of fluid. Typically, the body of fluid is clarified sewage that is directed through a conduit or channel within which the UV light apparatus, when adapted to a modular configuration, is inserted. Rather than have the ballasts and electronics that power and operate the UV lamps disposed externally of the apparatus in a remote location, which presents logistical problems associated with excessive wiring, time consuming maintenance and downtime, the apparatus according to the invention integrates the UV lamps with the ballasts and electronics, by segregating the ballasts and electronics into separate compartments for easy access and handling. This is an important design feature in that individual components of the UV light apparatus can be maintained, repaired or replaced without disturbing the other components of the apparatus by the utilization of detachable electrical couplers. Such couplers are integrated with the wiring and cabling communicating between the various components, viz., ballasts, electronics and UV lamps. Moreover, maintenance can be accomplished while the apparatus is on site in its operating environment. In addition, all of the components of the apparatus, or the entire apparatus itself, can be accessed or removed without disturbing other similar or like units that are functioning in close proximity. As such, the UV light apparatus may be used in combination with like or similar apparatus for the purification of a fluid. Maximum use and operation of the UV light purification apparatus are thereby achieved.

Figure 1:
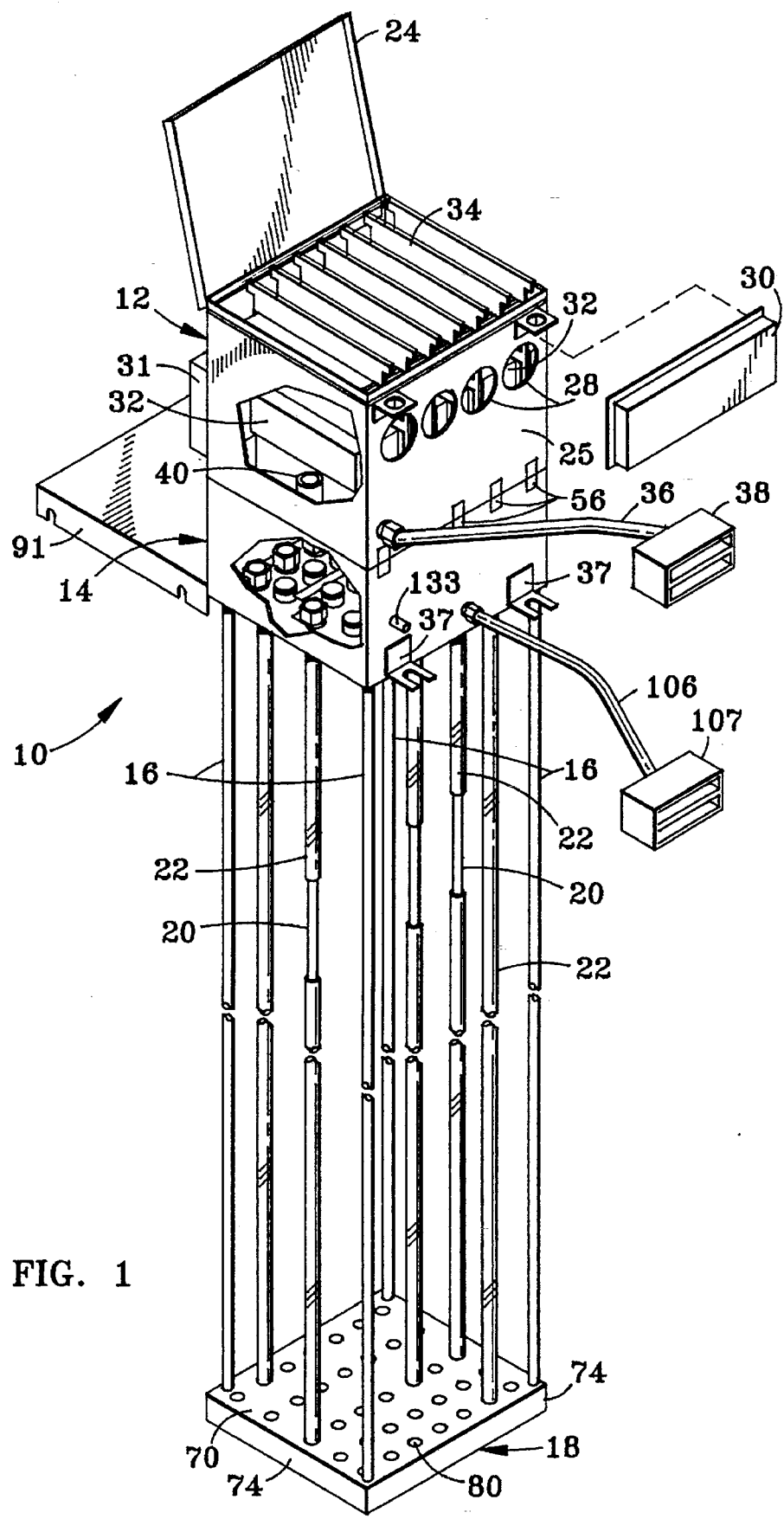
FIG. 1 illustrates an isometric perspective view of a fluid purification module in accordance with the invention herein.
Figure 3:
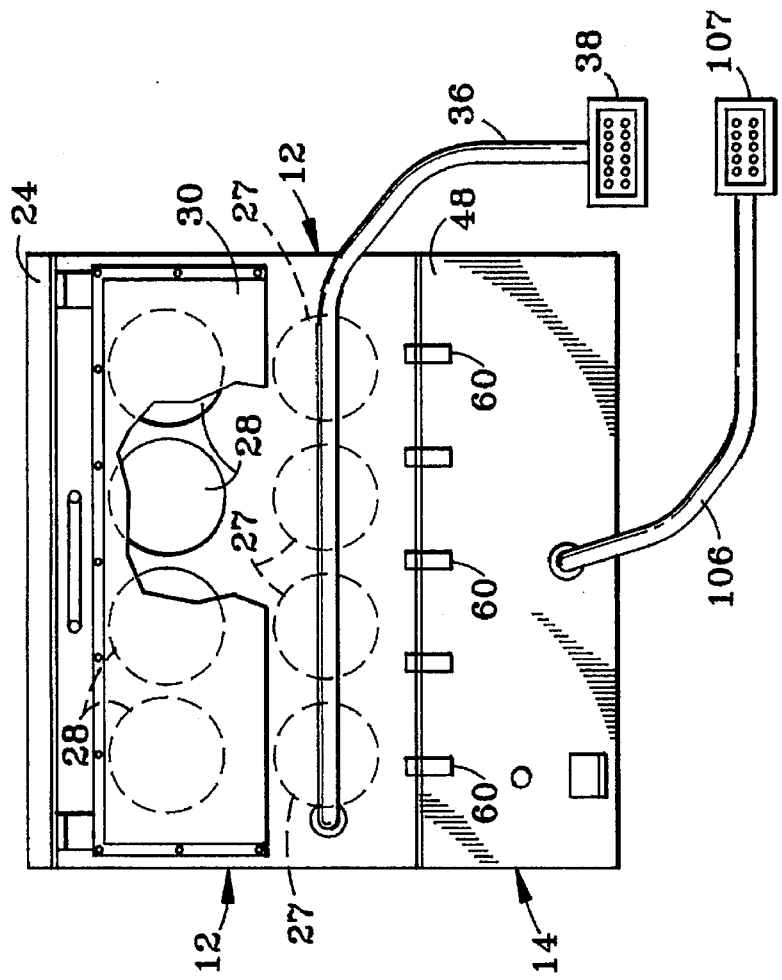
FIG. 3 is an elevated side view of the upper portion of the fluid purification module illustrating the compartments shown in FIG. 2.
Figure 2:
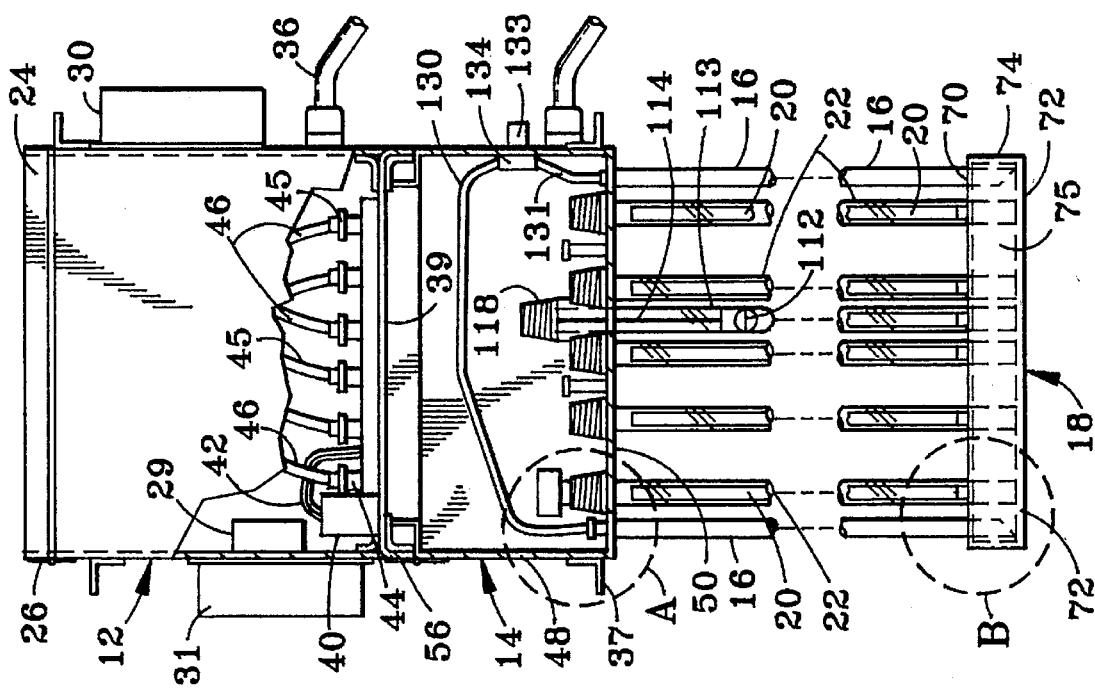
FIG. 2 is an elevated segmented and partial cross-sectional plan view of a major portion of the fluid purification module shown in FIG. 1.

Referring now to FIGS. 1, 2 and 3, a UV light purification apparatus is illustrated in the form of a module 10 constituting a preferred embodiment of the invention. The module comprises a stainless steel top compartment 12 overlying and interfacing a lower compartment 14 which is supported by a plurality of support legs 16 mounted to a support base 18. A plurality of transparent quartz sleeves 22 having corresponding UV lamps 20 inserted therein, are positioned between and mounted to support base 18 and the underlying portion of the lower compartment 14 in a manner that is described in greater detail below.

The top compartment 12 is provided with a cover 24 that has a hinge 26 (FIG. 2) for enabling the cover to be swung open in the manner shown in FIG. 1. Compartment 12 houses a plurality of ballasts 32 connected to alignment plates 34 for the separation and alignment of the ballasts within the compartment. Ballasts 32, which are used for powering UV lamps 20, are connected to a cable 36 configured to exit compartment 12 and terminate in a multi-pin electrical coupler 38 which communicates with a source of electrical power contained within a control console in a manner that is described in greater detail below. Due to the amount of heat given off by the ballasts during the operation of UV lamps 20, a plurality of openings 28 are incorporated into one side 25 of compartment 12 overlaid by a shroud 30 that is open on one side. The opposite side of compartment 12 has similar openings 27 (see FIG. 3) which are also covered by a shroud 31 interfacing a fan 29 for drawing ambient air into the bottom of the compartment 12 interior. Electrical fan 29 which is mounted in the bottom interior of compartment 12 (see FIG. 2), directs the ambient air over the ballasts which then exits through openings 28. A filter (not shown) can also be provided within shroud 31 to prevent unwanted foreign objects, e.g., insects, from entering the interior of compartment 12.

As an alternative to electrical fan 29, an air-conditioning or heat exchanger unit may be operatively connected with compartment 12 for cooling the interior thereof. The location of such units can be remote, or affixed to compartment 12 in the location occupied by shrouds 30 and/or 31. The alternative arrangement would necessitate the replacement of compartment openings 27 and 28 with appropriate openings to accommodate such units. Appropriate seals (not shown) are provided to insulate top compartment 12 from ambient conditions with the same integrity offered by the seals described below for lower compartment 14.

The bottom of top compartment 12, which is shown with greater clarity in the embodiment illustrated in FIG. 2, is coincident with the top of lower compartment 14. In other words, dividing wall 39 is common to both the top and lower compartments. Dividing wall 39 is provided with an electrical wire conduit 40 for the passage therethrough of electrical wires 42 leading from receptacles 44 that are provided with detachable couplers 45, which in turn receive lead wires 46 from the corresponding ballasts 32. With this arrangement any one of ballasts 32 can be removed from compartment 12 without disturbing the electrical connections of the other ballasts and the electrical connections to the electronics contained in lower compartment 14. In order to provide a water-tight seal for the interior of lower compartment 14, any means known in the art may be used to close electrical wire conduit 40, preferably with an annular seal (not shown) in the form of an "O" ring mounted on top of the inlet about which a threaded sleeve is provided to insure a proper seal about the wires passing through the "O" ring and wire conduit 40. It will be understood that in place of common dividing wall 39, the top and lower compartments can be configured for separation from one another.

Figure 4:
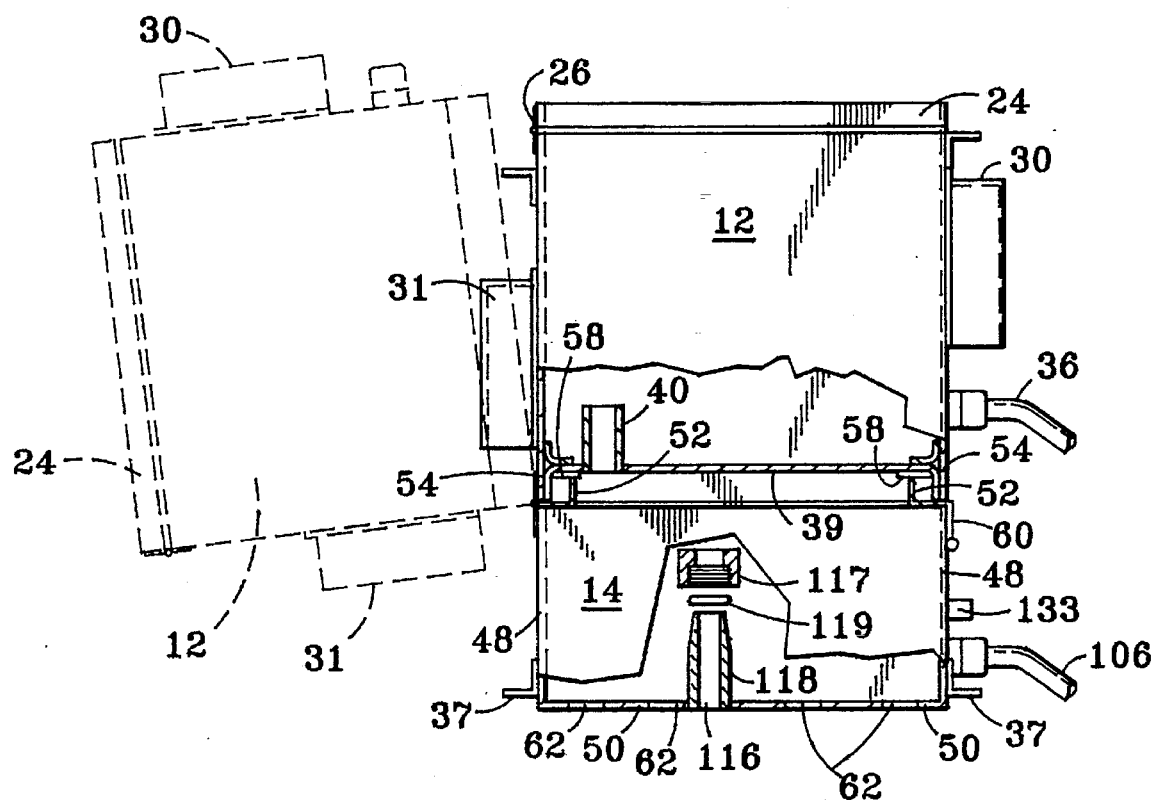
FIG. 4 is an elevated cross-sectional view of the upper portion of the fluid purification module shown in FIG. 3 illustrating an embodiment for the hinged removal of the top compartment of the module.

Referring to FIG. 4, lower compartment 14 has a box-like construction, preferably made of stainless steel, that includes side walls 48 and bottom member 50, to form a separate enclosure for the electronics used to operate UV lamps 20. The tops of side walls 48 are provided with indented extension walls 52 that are configured to be received within depending walls 54 extending downwardly from top compartment 12 and dividing wall 39. This arrangement enables top compartment 12, including the dividing wall 39, to be swung open in the manner illustrated in FIG. 4 by the provision of a hinge 56 fixed to the exterior of depending walls 54 and side walls 48. A seal 58, e.g., rubber or neoprene stripping, is fastened to the underside of dividing wall 39 along the perimeter thereof such that when top compartment 12 is lowered onto lower compartment 14, seal 58 will make compression contact with the top of indented side walls 52 when the top and bottom compartments are secured by a plurality of latches 60. In this manner, a water-resistant or waterproof seal may be provided to the interior of lower compartment 14, depending on the materials used which are well known in the art. Any material commonly known in the art can be used for the seal that will produce the desired effect, i.e., a water-resistant or waterproof seal. The term "water-resistant", as used herein, is consistent with the description offered by the National Electrical Manufacturers Association (NEMA Standard 250) for an enclosure that has a 4X classification, i.e., the enclosure is intended for indoor or outdoor use primarily to provide a degree of protection against corrosion, windblown dust and rain, splashing water, and hose-directed water, undamaged by the formation of ice on the enclosure. The term "waterproof" is consistent with the NEMA 6 classification, i.e., enclosures intended for use indoors or outdoors where occasional submersion is encountered.

Figure 5:
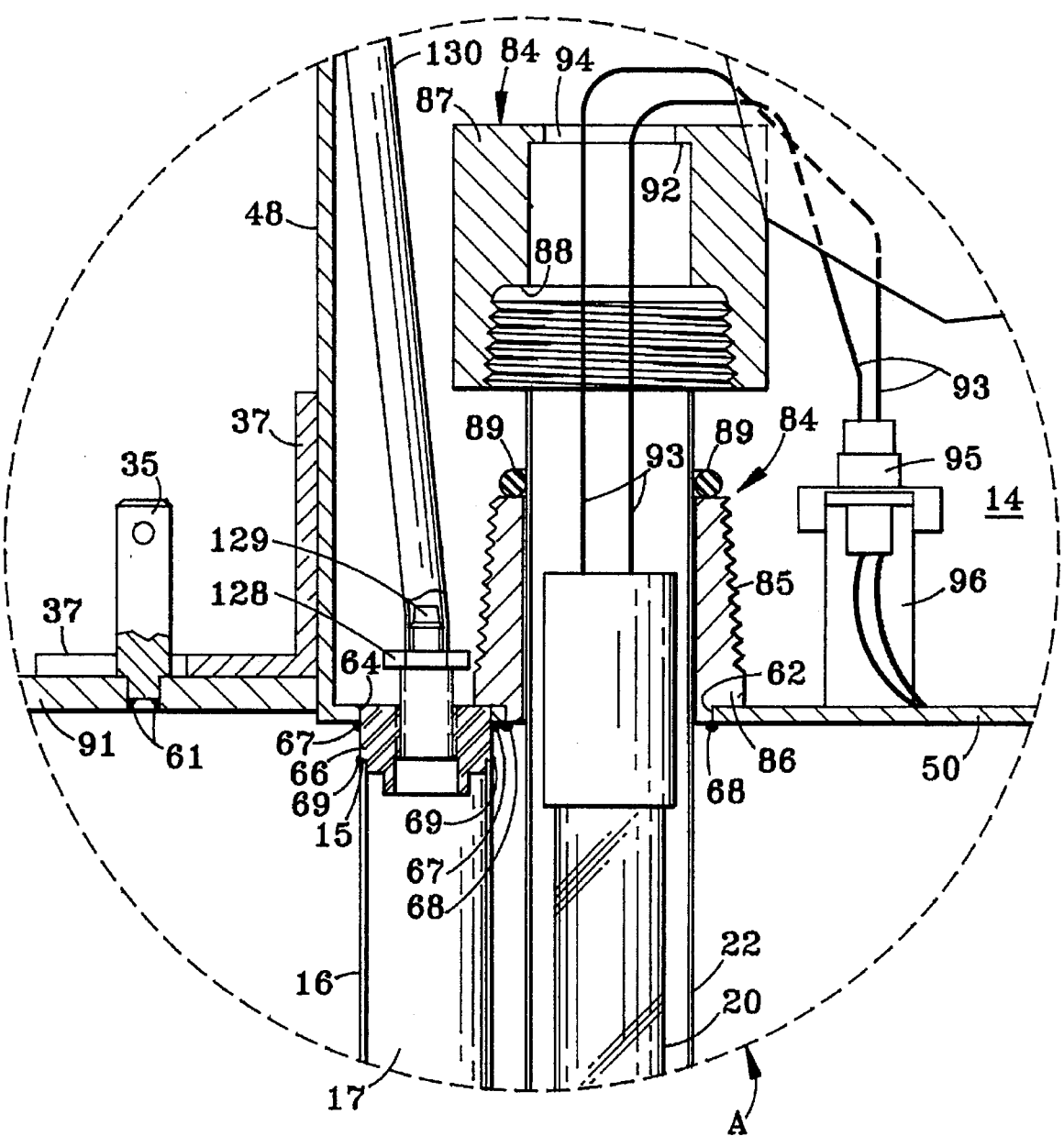
FIG. 5 is an elevated cross-sectional plan view on an enlarged scale of the circled detail identified by the letter A in FIG. 2, which illustrates the leg support and UV lamp and protective sleeve connection with the lower compartment of the module in accordance with an embodiment of the invention.
Figure 6:
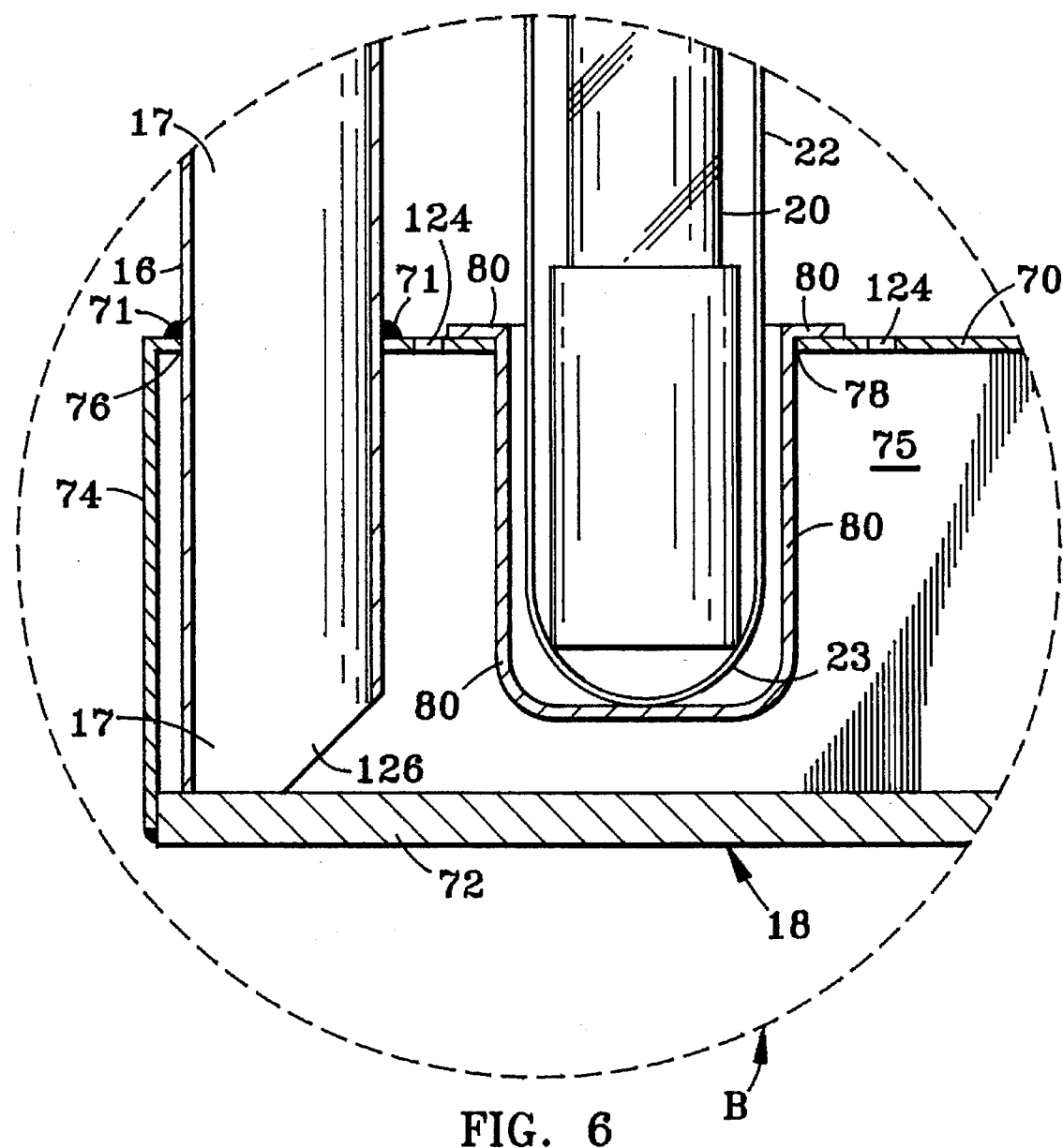
FIG. 6 is a cross-sectional plan view on an enlarged scale of the circled detail identified by the letter B in FIG. 2, which illustrates a leg support and a UV lamp and protective sleeve connection with the base of the module in accordance with an embodiment of the invention.

As illustrated in FIGS. 1, 5 and 6, transparent quartz sleeves 22 are configured in length and diameter to surround their corresponding UV lamps 20 for fully enclosing the same. The bottom of sleeve 22 extends beyond UV lamp 20 and is closed, while the opposite top end is open and also extends beyond the end of lamp 20 into a sleeve opening 62 of bottom member 50. Bottom member 50 of lower compartment 14 is provided with a plurality of such openings for receiving a corresponding number of transparent quartz sleeves 22 therethrough. Support leg openings 64 are located in the corners of bottom member 50 for receiving collars 66, which have the configuration of a half coupling and are fixed to bottom member 50 by a weld 67. Each collar 66 is secured to and rests on the top portion 15 of support leg 16 by means of a weld 69 to secure support legs 16 to bottom member 50 of lower compartment 14.

As will be seen in FIG. 6, support base 18 has a compartmentalized configuration that includes a top member 70 and bottom member 72 which are separated and joined at their perimeters by side walls 74 to provide a hollow interior 75. Top member 70 also includes support leg openings 76 located at the corners thereof for receiving support legs 16 therethrough into resting contact with the interior face of bottom member 72. Support legs 16 are secured within their respective openings 76 by welding the perimeter of leg 16 to top member 70 at 71. Top member 70 has a plurality of sleeve openings 78 for the insertion of cylindrical sleeve retainers 80 that are closed at one end and open at the opposite end for receiving the closed end 23 of corresponding transparent quartz sleeves 22 therein. The bottom portion of sleeves 22 are slidably received within their respective retainers 80 to prevent the lateral movement of UV lamp 20 and sleeve 22 within top member 70 of support base 18.

The waterproof coupling of sleeve 22 and UV lamp 20 within lower compartment 14 is best illustrated in FIG. 5. As noted herein, bottom member 50 has a plurality of openings 62 to permit the insertion of corresponding sleeves 22 therethrough. A waterproof compression fitting 84 is provided that includes a stainless steel threaded nipple 85 having a flange 86 at the base thereof. Flange 86 rests on bottom member 50 and is configured to fit within opening 62 where it is welded at 68 to provide a water-proof seal between the nipple flange 86 and bottom member 50. The open end of sleeve 22 extends through the top of nipple 85. A threaded gland nut 87, preferably made of a hardened plastic material, e.g., polyvinylchloride, is provided for engagement with nipple 85 to accomplish the waterproof compression fit. Gland nut 87 has an opening 94 whose diameter is slightly less than the internal diameter of sleeve 22 but greater than the outside diameter of UV lamp 20, and an internal shoulder 92 for axially containing the top portion of sleeve 22 within the confines of gland nut 87. Gland nut 87 is also provided with an internal shoulder 88 for engagement with an O-ring 89 such that when the gland nut is positioned about the top end of sleeve 22 and threaded onto nipple 85, the combination insures the insulation of UV lamp 20 and the interior of lower compartment 14 from the fluid to be treated. With this type of fitting, only the detachable coupler 95 needs to be disconnected from its corresponding connector bracket 96 to allow UV lamp 20 to be lifted and removed from its quartz sleeve.

It will be understood that only the quartz sleeves 22, UV lamps 20 and support base 18 of module 10 are designed for insertion into a body of fluid, such as in channel 90 having waste water flowing therethrough (see FIG. 8), for subjecting the fluid to the irradiation emitted by UV lamps 20. It is preferred, therefore, that lower compartment 14 not be immersed in the fluid during the normal course of operation of module 10. However, in order to protect the electronics contained within lower compartment 14, waterproof seals, as described herein, are highly desirable for the various openings contained in compartment 14 in the event that the compartment becomes immersed in the fluid if channel 90 suddenly overflows.

Because of the intensity of light emitted by UV lamps 20, and the desire to protect the human eye therefrom during the operation of module 10, the lower portion of bottom compartment 14 is provided with L-shaped mounts 37 (FIGS. 1 and 5) for attachment to a light shield 91 that is placed over channel 90 (FIG. 8) adjacent to module 10. Engagement of the mounts, with the light shield is accomplished by placing the mounts, which are provided with laterally opened slots (FIG. 1), over vertically extending attachment studs 35, incorporated and welded at 61 into shield 91, when module 10 is inserted into channel 90.

As a preference, the UV lamps used in module 10 are low pressure mercury lamps which provide an ultraviolet light transmission of approximately 185 or 253.7 nanometers. Each UV lamp has a pair of lead wires 93 leading through opening 94 in gland nut 87 and terminating in a detachable coupler 95 that detachably inserts into a corresponding 2-pin connector bracket 96 mounted to bottom member 50. It will be readily seen that sleeves 22 and UV lamps 20 can be easily removed by unhooking latches 60, swinging top compartment 12 to an open position (as shown by the broken lines in FIG. 4), detaching coupler 95, and lifting the lamp and sleeve through its corresponding compression fitting 84. The servicing of each UV lamp 20 within module 10 can therefore be accomplished without the prerequisite of removing ballasts 32 or other electrical components, which are described in greater detail below, or for that matter, without removing module 10 from the body of fluid under treatment. Greater efficiency and economy for maintaining and servicing the module is thereby achieved.

Figure 7:
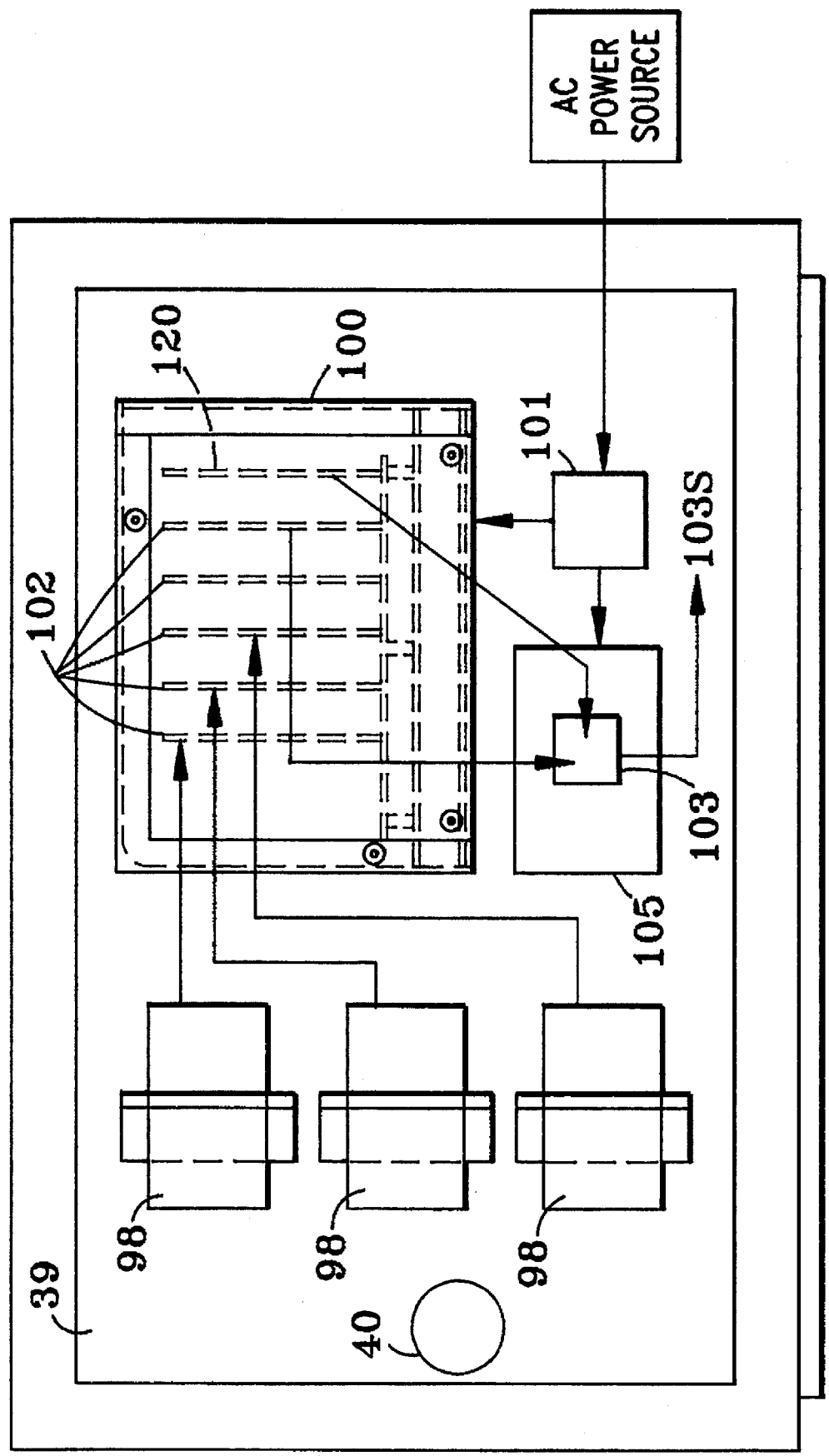
FIG. 7 is an enlarged schematic plan view of the interior of the lower compartment of the module illustrated in FIG. 1 selectively illustrating the electronics housed therein in accordance with an embodiment according to the invention.
Figure 8:
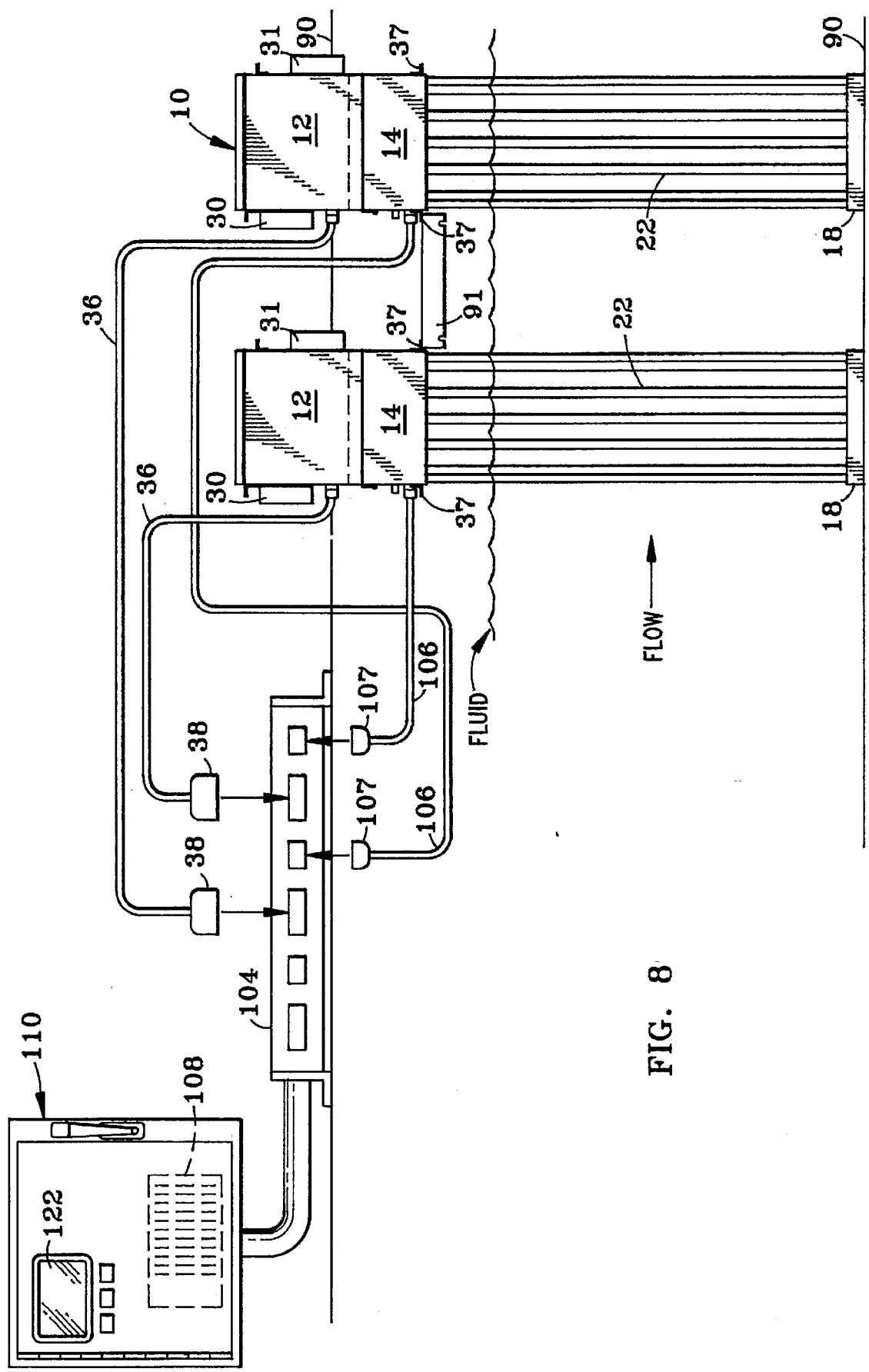
FIG. 8 is a schematic diagram illustrating a manner of controlling the operation of a the fluid purification module shown in FIG. 1 in accordance with one embodiment of the invention.

Various electronics can be incorporated into lower compartment 14 of module 10 to facilitate the operation and control of UV lamps 20. As already noted hereinbefore under the Summary Of Invention heading, the apparatus according to the invention may optionally include a means for sensing the functional status of the UV lamps employed therein. Referring to FIG. 7, a plurality of electrical coils 98 mounted to the underside of dividing wall 39 in lower compartment 14 are provided for sensing the electric current transmitted to UV lamps 20 by ballasts 32 during the lamps' operation. Also provided to the underside of dividing wall 39 is a backplane receptacle 100 which receives power through an AC/DC converter 101 derived from an AC source within control console 110 (FIG. 8). Backplane receptacle 100 is operatively connected to electrical coils 98 by means of a ribbon cable (not shown) for receiving a signal from the coils reflecting the ON/OFF status of each UV lamp 20. Backplane receptacle 100 comprises a plurality of electrical slots (not shown) for receiving therein a corresponding number of electronic lamp status circuit boards 102 whose function is to receive the signal generated by coils 98 and convert the signal from an analog signal to a digital signal (A/D converter) for transmission to a processing means in the form of an operatively connected microprocessor 103. Each lamp status circuit board 102 is designed to receive any number of signals from coils 98 reflecting the status of up to eight UV lamps utilized in the module per coil.

Microprocessor 103 is contained within a module interface board 105 which also receives its power through AC/DC convertor 101. Each lamp status circuit board 102 is operatively connected to microprocessor 103. Once the parallel data signals reflective of the ON/OFF status of UV lamps 20 are received by microprocessor 103, the serial data signals 103S generated within microprocessor 103 are transmitted to a remotely located wireway 104 (see FIG. 8) via a cable 106 that has a multi-pin connector 107 at one end thereof (see also FIG. 3) for attachment to the wireway, which in turn relays the serial data signals to a programmable logic controller 108 housed in a remotely located control console 110 for controlling the operation of module 10.

In another aspect of the invention, module 10 may also include a UV light sensor 112 housed in a tubular enclosure 113 that depends from bottom member 50 of lower compartment 14 (see FIG. 2). Sensor 112 responds to the germicidal wavelength portion of the wavelength emitted from UV lamps 20, and will detect any change in UV light intensity, typically a decrease, as the result of the accumulation of fluid debris on the surface of the transparent quartz sleeves 22. Accordingly, sensor 112 is preferably positioned intermediate the support base 18 and lower compartment 14 for sensing the intensity of ultraviolet light generated by the UV lamps 20 surrounding the sensor.

Referring to FIGS. 2 and 4, in order to accommodate the lead wires 114 leading from sensor 112 to the interior of lower compartment 14, tubular enclosure 113 extends through opening 116 and into a stainless steel threaded nipple 118 welded to bottom member 50 (FIG. 4) in waterproof relationship thereto in the same manner as threaded nipple 85 of compression fitting 84 illustrated in FIG. 5. A gland nut 117, also preferably made of a hardened plastic material such as polyvinylchloride and having an internal shoulder engaged with an O-ring 119, is threaded onto nipple 118 for accomplishing a waterproof compression fit. Sensor lead wires 114 are connected to backplane receptacle 100 (FIG. 7) which is provided with a slot (not shown) for the receipt therein of a UV light sensor board 120 that converts the electrical signal from sensor 112 to a logic level (A/D converter). The logic level signal containing parallel data is then transmitted to microprocessor 103 which in turn generates and transmits a UV sensor serial data signal that is transmitted with serial data signals 103S to the programmable logic controller 108 contained within control console 110 via wireway 104. The intensity of the ultraviolet light sensed by sensor 112 can then be displayed by appropriate electronics readily known in the art onto a local operator interface screen 122 located in control console 110.

Remotely located control console 110, through the use of appropriate electronics (which do not form a part of the invention herein), permits an operator to monitor and control UV light purification module 10, or a plurality of such modules, either automatically or manually, by receiving and interpreting the signals from lamp status circuit boards 102 and UV light sensor board 120. This information will assist an operator in determining the proper amount of fluid flow passing by module, 10 which is accomplished by monitoring the incoming fluid flow into channel 90 through the use of adjustable electrically monitored fluid level indicators (not shown). The information will ultimately assist the operator in determining the number of UV lamps required for the purification of the fluid at a given flow rate or fluid level in channel 90.

In order to assist in the prevention of the accumulation of fluid debris onto the surface of sleeves 22, and in accordance with another aspect of the invention, module 10 can be provided with a means for preventing the collection of contaminants or debris onto the sleeve surface. Once again referring to FIG. 6, top member 70 of support base 18 is provided with a plurality of apertures 124 surrounding and proximate to each sleeve retainer 80. Support leg 16 has a tubular construction such that a conduit 17 is disposed within the entire length thereof. Communication between conduit 17 and hollow interior 75 of support base 18 is provided by removing a section of leg 16 in the manner illustrated in FIG. 6 to provide a support leg opening 126.

Referring to FIG. 5, and as already noted herein, collar 66 is inserted into the top opening 15 of support leg 16 with a weld 69. A properly configured hollow threaded compression fitting 128 is threaded into collar 66 such that a fluid tight seal is secured between the head of compression fitting 128 and the threaded axial opening of collar 66. The opposite end of compression fitting 128 is provided with a hollow stainless steel nipple 129 for forcible insertion into flexible tubing 130 to obtain a fluid tight seal between support leg 16 and tubing 130. As shown in FIG. 2, a similar arrangement is provided for support leg 16 supporting the opposite end of lower compartment 14 using an identical flexible tubing 131.

The opposite end of flexible tubing 130 is secured to a four way compression fitting 134 threaded to a housing 133 that is welded to the side wall 48 of lower compartment 14. A source of compressed air (not shown) is coupled with housing 133 via an appropriate conduit (also not shown). In operation, compressed air is introduced to lower compartment 14 via fitting 134 and housing 133, and communicated to the hollow interior 75 of support base 18 through flexible tubings 130 and 131 and conduits of support legs 16. After entry into the hollow interior 75 of support base 18, the air, still under pressure, will escape through apertures 124 of top member 70 in the form of air bubbles which will have the effect of agitating the fluid flowing past quartz sleeves 22 thereby preventing the accumulation of contaminants and debris onto the surface of quartz sleeves 22.

As an alternative to the aforestated prevention means, or in addition thereto, the module may optionally include a means for cleaning or wiping the exterior surface of the quartz sleeves 22 surrounding UV lamps 20. The cleaning means generally comprises a mechanical wiping system which includes at least one disc comprising a plurality of openings, each opening conforming to the corresponding cross-sectional configuration of quartz sleeves 22 and being lined with a means for wiping the sleeves, e.g., by bristles or a sponge-like material. The quartz sleeves are received through their respective openings in the disc and are wiped when the disc is slidably moved along the axis of the quartz sleeves. Such a wiping system further includes a means for causing the disc to move in either direction along the axis of the quartz sleeves 22 thereby substantially removing the collection of contaminants and residue formed thereon by the fluid. The disc is preferably axially connected to one end of a shaft whose opposite end is operatively connected to a means for causing the piston to axially move in either direction, e.g., by means of an electrically, pneumatically or hydraulically driven solenoid-operated piston communicating with the shaft. A housing containing the piston can be mounted to the support base 18, although it is preferably mounted to the underside of member 50 of lower compartment 14. A plurality of discs spaced apart from each other in the axial direction and mounted to the shaft, are preferably used.

The apparatus according to the invention provides an inexpensive and economical means by which the apparatus' individual components can be maintained, repaired or replaced without disturbing the other components. By arranging the individual operating components into separate functional compartments, on-site maintenance and/or removal of the components can be effected without the removal of the entire apparatus.

Since other modifications and changes may be varied to fit the particular operating requirements and environments of the invention, which will be apparent to those skilled in the art, the invention is not considered to be limited to the embodiments chosen for purposes of disclosure and illustration, and covers all changes and modifications which do not constitute departures from the true spirit and scope thereof.

What is claimed is:

1. An ultraviolet light apparatus for the purification of a fluid comprising a plurality of vertically arranged ultraviolet lamps;

means for permitting the lamps to be submerged in the fluid to be treated;

at least one ballast for powering said lamps;

at least one housing for containing the ballast therein;

electrical means providing communication between the ballast and lamps to permit operation of the lamps; and at least one enclosure disposed intermediate the housing and plurality of UV lamps for the containment of the electrical means therein, wherein each of the lamps is vertically aligned with said enclosure.

2. The apparatus defined by claim 1 wherein the housing, enclosure and plurality of lamps are vertically aligned relative to each other.

3. The apparatus defined by claim 2 wherein the housing and enclosure interface each other.

4. The apparatus defined by claim 1 wherein the apparatus is provided with a plurality of ballasts for powering said lamps.

5. The apparatus defined by claim 1 wherein the means for permitting the lamps to be submerged in the fluid includes a radiation pervious protective sleeve disposed about each lamp.

6. The apparatus defined by claim 5 wherein the sleeve is constructed of quartz, one end of which is closed and the other end secured within the enclosure in waterproof relationship thereto.

7. The apparatus defined by claim 1 wherein the enclosure is sealed to provide a water-resistant atmosphere for the electrical means therein.

8. The apparatus defined by claim 1 wherein the enclosure is provided with a waterproof seal to prevent the substantial entrainment of moisture therein.

9. The apparatus defined by claim 1 wherein the housing is provided with a means for cooling the ballast therein.

10. The apparatus defined by claim 9 wherein the means for cooling the ballast comprises at least one opening therein for the passage of ambient air into the housing.

11. The apparatus defined by claim 10 wherein the means for cooling the ballast additionally comprises at least one fan operatively communicating with the opening for the circulation of ambient air into the housing.

12. The apparatus defined by claim 11 wherein the housing is provided with a plurality of openings on opposite sides thereof for the passage of ambient air through the housing.

13. The apparatus defined by claim 10 wherein the means for cooling the ballast comprises an air conditioning means or heat exchanger means communicating with the opening in the housing.

14. The apparatus defined by claim 1 wherein the apparatus is provided with a base communicating with a plurality of vertically arranged support legs communicating with the enclosure for supporting the lamps between the enclosure and base.

15. The apparatus defined by claim 1 wherein the electrical means includes lead wires connecting the lamps with detachable couplers disposed within the enclosure.

16. The apparatus defined by claim 1 wherein the ballast includes lead wires communicating with detachable couplers disposed within the housing for detachably connecting the ballast to the electrical means.

17. The apparatus defined by claim 1 wherein the electrical means includes means for generating a signal that is reflective of the functional status of at least one lamp contained within the apparatus.

18. The apparatus defined by claim 1 wherein a sensing means is provided intermediate the base and enclosure for sensing the intensity of ultraviolet light generated by said lamps.

19. The apparatus defined by claim 18 wherein the electrical means includes means for generating a signal that is reflective of the intensity of the ultraviolet light detected by the sensing means.

20. An ultraviolet light module for the purification of a fluid, comprising
   a plurality of vertically arranged ultraviolet lamps;
   means for permitting the lamps to be submerged in the fluid to be treated;
   a plurality of ballasts for powering said lamps;
   at least one housing for containing the ballasts therein;
   electrical means providing communication between the ballasts and lamps to permit operation of the lamps;
   at least one enclosure disposed intermediate the housing and plurality of UV lamps for the containment of the electrical means therein; and
   a base communicating with a plurality of vertically arranged support legs communicating with the enclosure for supporting the lamps between the enclosure and base;
wherein each of the lamps is vertically aligned with said enclosure.

21. The module defined by claim 20 wherein the housing, enclosure and plurality of lamps are vertically aligned relative to each other.

22. The module defined by claim 21 wherein the housing and enclosure interface each other.

23. The module defined by claim 20 wherein the means for permitting the lamps to be submerged in the fluid includes a radiation pervious protective sleeve disposed about each lamp.

24. The module defined by claim 23 wherein the sleeve is constructed of quartz, one end of which is closed and the other end secured to the receptacle in waterproof relationship thereto.

25. The module defined by claim 20 wherein the enclosure is sealed to provide a water-resistant atmosphere for the electrical means therein.

26. The module defined by claim 20 wherein the enclosure is provided with a waterproof seal to prevent the substantial entrainment of moisture therein.

27. The module defined by claim 20 wherein the housing is provided with a means for cooling the ballasts therein.

28. The module defined by claim 27 wherein the means for cooling the ballasts comprises at least one opening therein for the passage of ambient air into the housing.

29. The module defined by claim 28 wherein the means for cooling the ballasts additionally comprises at least one fan operatively communicating with the opening for the circulation of ambient air into the housing.

30. The module defined by claim 29 wherein the housing is provided with a plurality of openings on opposite sides thereof the passage of ambient air through the housing.

31. The module defined by claim 28 wherein the means for cooling the ballasts comprises an air conditioning means or heat exchanger means communicating with the opening in the housing.

32. The module defined by claim 20 wherein the electrical means includes lead wires connecting the lamps with detachable couplers disposed within the enclosure.

33. The module defined by claim 20 wherein the ballasts include lead wires communicating with corresponding detachable couplers disposed within the housing for detachably connecting the ballasts to the electrical means.

34. The module defined by claim 20 wherein the electrical means includes means for generating a signal that is reflective of the functional status of at least one lamp contained within the apparatus.

35. The module defined by claim 20 wherein a sensing means is provided intermediate the base and enclosure for sensing the intensity of ultraviolet light generated by said lamps.

36. The module defined by claim 35 wherein the electrical means includes means for generating a signal that is reflective of the intensity of the ultraviolet light detected by the sensing means.

37. The module defined by claim 20 which additionally includes means for agitating the fluid about the lamps, said means comprising at least one aperture provided in the base of the module about at least one of said lamps communicating with a source of compressed gas for the passage of the gas through said aperture.

38. The module defined by claim 37 wherein a plurality of apertures are provided in the base of the module.

39. The module defined by claim 37 wherein at least one support leg serves as a conduit for the passage of the compressed gas to said base.

40. The module defined by claim 39 wherein the compressed gas is introduced to the leg support from a source external to the module via a conduit provided in the enclosure communicating with the leg support.

41. An apparatus for powering the operation of a plurality of vertically arranged ultraviolet lamps immersed in a fluid for the treatment thereof comprising
    at least one housing containing a plurality of ballasts therein for powering said lamps; and
    at least one enclosure disposed intermediate the housing and plurality of lamps for the containment therein of electrical means for operating said lamps;
wherein the housing and enclosure are substantially vertically aligned relative to each other.

42. The apparatus defined by claim 41 wherein the housing and enclosure interface each other.

43. The apparatus defined by claim 41 wherein the enclosure is sealed to provide a water-resistant atmosphere for the electrical means therein.

44. The apparatus defined by claim 41 wherein the enclosure is provided with a waterproof seal to prevent the substantial entrainment of moisture therein.

45. The apparatus defined by claim 41 wherein the housing is provided with a means for cooling the ballasts therein.

46. The apparatus defined by claim 45 wherein the means for cooling the ballasts comprises at least one opening therein for the passage of ambient air into the housing.

47. The apparatus defined by claim 46 wherein the means for cooling the ballasts additionally comprises at least one fan operatively communicating with the opening for the circulation of ambient air into the housing.

48. The apparatus defined by claim 46 wherein the housing is provided with a plurality of openings on opposite sides thereof for the passage of ambient air through the housing.

49. The apparatus defined by claim 46 wherein the means for cooling the ballast comprises an air conditioning means or heat exchanger means communicating with the opening in the housing.

50. The apparatus defined by claim 41 wherein the electrical means includes lead wires connecting the lamps with detachable couplers disposed within the enclosure.

51. The apparatus defined by claim 41 wherein the ballasts include lead wires communicating with corresponding detachable couplers disposed within the housing for detachably connecting the ballasts to the electrical means.

52. The apparatus defined by claim 41 wherein the electrical means includes means for generating a signal that is reflective of the functional status of at least one of the ultraviolet lamps.

53. The apparatus defined by claim 41 wherein a sensing means is provided below the enclosure for sensing the intensity of ultraviolet light generated by said lamps.

54. The apparatus defined by claim 53 wherein the electrical means includes means for generating a signal that is reflective of the intensity of the ultraviolet light detected by the sensing means.

55. In combination,
    means comprising a body of fluid to be purified;
    an ultraviolet light fluid purification module for incorporation into the body of fluid, comprising
    a plurality of vertically arranged ultraviolet lamps positioned in the body of fluid;
    a plurality of ballasts for powering the lamps;
    at least one housing for containing the ballasts therein;
    electrical means providing communication between the ballasts and lamps to permit operation of the lamps;
    at least one enclosure disposed intermediate the housing and plurality of UV lamps for the containment of the electrical means therein; and
    a base communicating with a plurality of vertically arranged support legs communicating with the enclosure for supporting the lamps between the enclosure and base;
wherein the housing, enclosure and plurality of lamps are vertically aligned relative to each other.

56. The combination defined by claim 55 wherein a plurality of modules are positioned in the body of fluid to be treated.

57. The combination defined by claim 55 wherein the housing and enclosure interface each other.

58. The combination defined by claim 55 wherein the module includes means for permitting the lamps to be submerged in the fluid.

59. The combination defined by claim 58 wherein the means for permitting the lamps to be submerged in the fluid includes a radiation pervious protective sleeve disposed about each lamp, one end of which is closed and the other end secured to the enclosure in waterproof relationship thereto.

60. The combination defined by claim 59 wherein the sleeve is constructed of quartz.

61. The apparatus defined by claim 2 wherein the housing includes a top cover, side walls, and a bottom wall, and the enclosure includes a top cover, side walls, and a bottom wall.

62. The apparatus defined by claim 61 wherein the top cover of the housing is removable.

63. The apparatus defined by claim 61 wherein the top cover of the enclosure is removable.

64. The apparatus defined by claim 61 wherein the bottom wall of the housing and the top cover of the enclosure are common to each other and define a dividing wall.

65. The apparatus defined by claim 64 wherein the dividing wall is removable from the enclosure.

66. The apparatus defined by claim 65 wherein the dividing wall is connected to the housing and is removable from the enclosure by hinge means secured to a side wall of the housing and enclosure.

67. The module defined by claim 21 wherein the housing includes a top cover, side walls, and a bottom wall, and the enclosure includes a top cover, side walls, and a bottom wall.

68. The module defined by claim 67 wherein the top cover of the housing is removable.

69. The module defined by claim 67 wherein the top cover of the enclosure is removable.

70. The module defined by claim 67 wherein the bottom wall of the housing and the top cover of the enclosure are common to each other and define a dividing wall.

71. The module defined by claim 70 wherein the dividing wall is removable from the enclosure.

72. The module defined by claim 71 wherein the dividing wall is connected to the housing and removable from the enclosure by hinge means secured to a side wall of the housing and enclosure.

73. The apparatus defined by claim 41 wherein the housing includes a top cover, side walls, and a bottom wall, and the enclosure includes a top cover, side walls, and a bottom wall.

74. The apparatus defined by claim 73 wherein the top cover of the housing is removable.

75. The apparatus defined by claim 73 wherein the top cover of the enclosure is removable.

76. The apparatus defined by claim 73 wherein the bottom wall of the housing and the top cover of the enclosure are common to each other and define a dividing wall.

77. The apparatus defined by claim 76 wherein the dividing wall is removable from the enclosure.

78. The apparatus defined by claim 77 wherein the dividing wall is connected to the housing and removable from the enclosure by hinge means secured to a side wall of the housing and enclosure.

* * * * *